United States Patent [19]
Valbert

[11] Patent Number: 6,002,030
[45] Date of Patent: Dec. 14, 1999

[54] ESTERIFIED PROPOXYLATED POLYOL PROCESS

[75] Inventor: Jon R. Valbert, Arlington, Mass.

[73] Assignee: ARCO Chemical Technology, L.P., Greenville, Del.

[21] Appl. No.: 09/074,674

[22] Filed: May 8, 1998

[51] Int. Cl.⁶ ............................. C07H 13/06; C11C 3/00; A21D 2/16

[52] U.S. Cl. ...................... 554/124; 554/149; 554/148; 554/167; 554/168; 536/18.6

[58] Field of Search ................................. 55/20, 27, 28, 55/30, 31; 554/84, 149; 260/410.6, 410.7

[56] References Cited

U.S. PATENT DOCUMENTS

| | | | |
|---|---|---|---|
| 3,633,340 | 1/1972 | Illingworth | 55/84 |
| 3,999,963 | 12/1976 | Ririe, Jr. | 55/51 |
| 4,861,613 | 8/1989 | White et al. | |
| 4,983,329 | 1/1991 | Cooper. | |
| 5,571,935 | 11/1996 | Sekula et al. | |
| 5,681,939 | 10/1997 | Ferenz. | |

*Primary Examiner*—James O. Wilson
*Assistant Examiner*—Howard Owens, Jr.
*Attorney, Agent, or Firm*—William C. Long

[57] ABSTRACT

A process is provided for the fatty acid esterification of propoxylated glycerin wherein fatty acids stripped from the esterifier and/or fatty acids stripped from the esterification product are scrubbed by contact with a scrubbing liquid which is maintained at a temperature above the fatty acid melting point.

5 Claims, 2 Drawing Sheets

ESTERIFIED PROPOXYLATED POLYOL PROCESS

BACKGROUND OF THE INVENTION

1. Field of the Invention

The present invention relates to the fatty acid esterification of propoxylated glycerin and to improved recovery of fatty acids from various vapor streams found in the system.

2. Description of the Prior Art

The preparation of esters of propoxylated polyols is known. A particularly important technology relates to the preparation of food grade quality esters of propoxylated glycerin as described, for example, in U.S. Pat. Nos. 4,983,329, 5,571,935, 5,681,939, and the like.

During the esterification reaction water is formed which must be removed in order to achieve high esterification conversion. Generally water removal is accomplished by stripping water of reaction from the esterification reactor by nitrogen stripping and/or by carrying out the reaction under vacuum conditions.

A certain amount of fatty acid is volatilized and removed with the water of reaction which causes problems in recovery procedures by virtue of the high melting point of the volatilized fatty acid. The high melting fatty acids tend to solidify on cold condensation surfaces causing severe heat transfer problems.

Similarly, the esterification reaction mixture, upon completion of the desired esterification, contains unreacted fatty acid which must be stripped from the ester. Problems are also encountered in the recovery of the stripped fatty acid due to the high fatty acid meeting point.

BRIEF DESCRIPTION OF THE INVENTION

In accordance with the invention, fatty acids in the vapor stripped from the esterifier during esterification and/or unreacted fatty acids stripped from the esterification reaction mixture on completion of the esterification are scrubbed therefrom with a scrubbing liquid maintained above the melting temperature of the fatty acids, preferably the scrubbing liquid is previously condensed fatty acid.

DESCRIPTION OF THE DRAWINGS

The accompanying drawings illustrate schematic practices of the invention.

DETAILED DESCRIPTION

Figure 1:
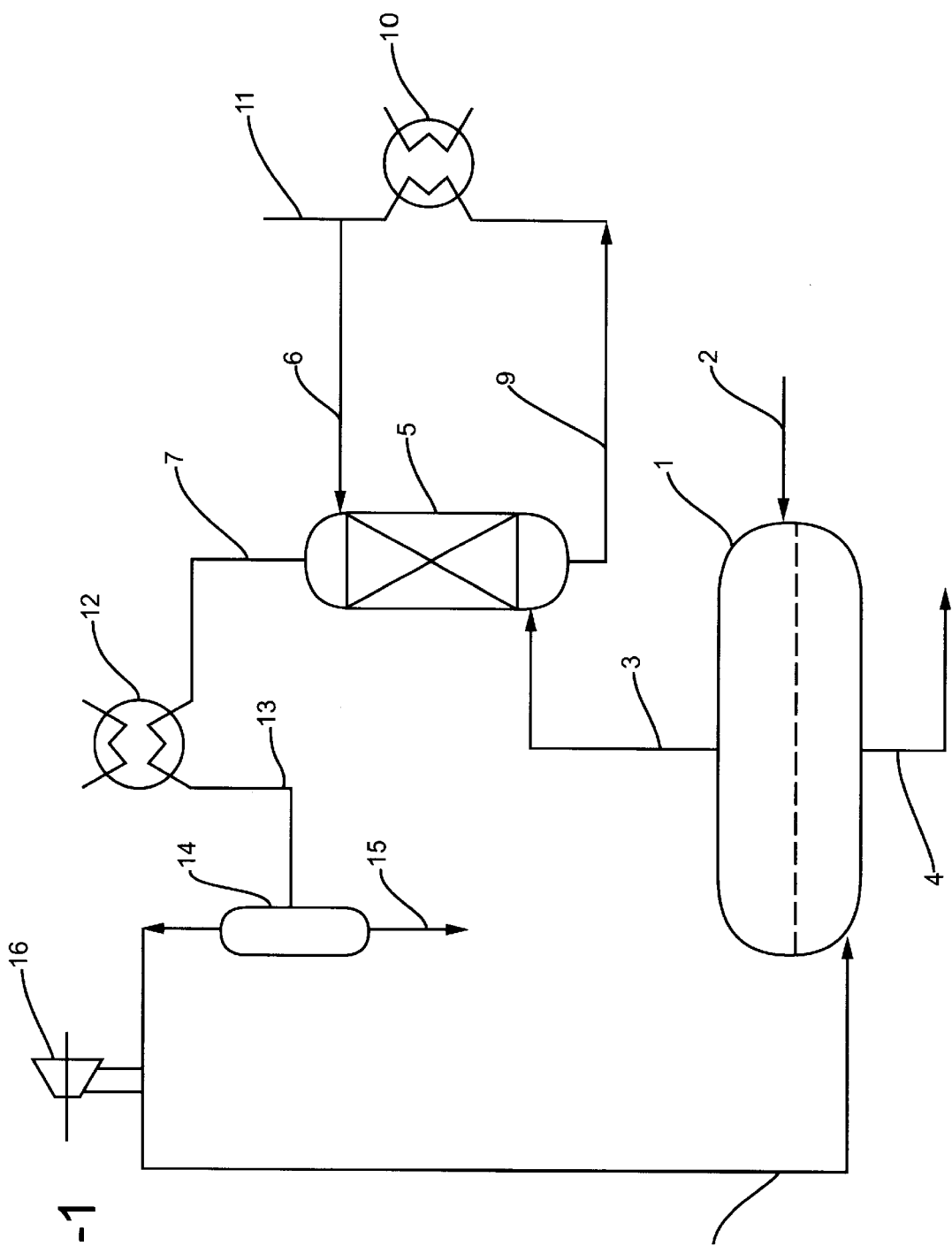
FIG. 1 deals with the recovery of fatty acids stripped from the esterifier during esterification while FIG. 2 deals with recovery of fatty acids from the esterification reaction mixture after completion of the esterification.

The esterification reaction of the invention is itself a known reaction. As described in U.S. Pat. No. 5,681,939, the propoxylated glycerin reactant employed may be prepared by any of the standard methods known in the art such as, for example, the base-catalyzed reaction of propylene oxide with glycerin. While the molar ratio of propylene oxide to glycerin is not critical, if the esterified propoxylated glycerin is to be used as a reduced calorie fat substitute it is preferred that from 2 to 20 more preferably 3 to 15, moles of epoxide be reacted per mole of glycerin. The propoxylation of glycerin can be carried out by the addition of propylene oxide to glycerin in the presence of a catalytic amount of an alkali metal alkoxylate at a temperature of from about 70° C. to 130° C. The alkali metal alkoxylate is desirably prepared by heating an alkali metal compound such as sodium hydroxide or potassium hydroxide with glycerin at an elevated temperature while continuously removing water, preferably under reduced pressure. Preferably, sufficient catalyst is present during propoxylation to provide an alkali metal content of about 0.0003 moles to 3.3 moles alkali metal per 100 g of glycerin. The propylene oxide is preferably fed incrementally into a reactor containing the glycerin and catalyst at a rate sufficient of maintain a pressure within the reactor of about 40 to 80 psia. The degree of propoxylation is controlled, and thus the molecular weight of the propoxylated glycerin as well, by regulating the amount of propylene oxide fed to the rector. After the desired molecular weight is reached, the alkali metal may be removed prior to esterification by any suitable method such as absorption, ion exchange, or extraction.

The propoxylated glycerin thus obtained will have a chemical structure generally as follows:

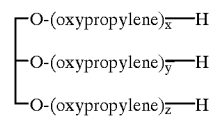

wherein x, y, and z are the same or different and are 0 or preferably an integer of from 1 to 20 with the sum of x+y+z preferably ranging from 2 to 20 (more preferably, 3 to 15). The oxypropylene units in the propoxylated glycerin have the structure

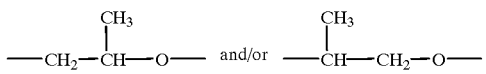

with the former type of structure preferably predominating.

The fatty acids which may be employed as reactants in the present invention may be saturated or unsaturated fatty acids or mixtures thereof. Straight chain as well as branched fatty acids may be used. Preferably, the fatty acid is a $C_{10}$–$C_{24}$ fatty acid (i.e., an acid which contains from 10 to 24 carbon atoms). An excess of fatty acid, preferably from 1 to 40% molar excess relative to the amount of propoxylated glycerin, is employed in the present process in order to catalyze the desired esterification such that the desired esterified propoxylated glycerin product may be rapidly obtained without adding other catalysts. Illustrative of the $C_{10}$–$C_{24}$ fatty acids which may be utilized are saturated acids such as capric, lauric, myristic, pentadecanoic, palmitic, heptadecanoic, stearic, nonadecanoic, eicosanoic, and behenic acid. Unsaturated fatty acids which are conveniently available by conventional splitting (hydrolysis) of natural and hydrogenated vegetable oils and animal fats are also appropriate for use such as, for example, soybean oil fatty acids, hydrogenated high erucic rapeseed oil fatty acids, coconut oil fatty acids and the like. A large excess of fatty acid need not be used, since minimal fatty acid will be lost from the reactor. The process may thus be advantageously performed with 10–25% molar excess fatty acid.

The propoxylated glycerin and the fatty acid are introduced into a reaction zone to form a reaction mixture. The component reactants may be added separately or, if so desired, first combined or blended prior to entering the reaction zone. The reaction mixture may initially be at a temperature of from about 80° C. to 120° C., and a pressure of from about 13 to 16 psia. The initial pressure, for example, may conveniently be atmospheric pressure and the initial temperature may be room temperature or, if needed to completely melt the reactants to form a homogeneous liquid phase, somewhat higher than room temperature. While the configuration and design of the reaction zone is not critical, a reactor vessel should be selected which is capable of heating and agitating (mixing) the contents of the vessel under subatmospheric pressure. Means for introducing the reactants and for removing the water of reaction as an overhead stream in vapor form from the vessel provided. It may be advantageous to utilize equipment which will provide high shear mixing (e.g., a 5 to 600 m/min. tip speed, which typically may be achieved by a drive motor energy input of 1.5 to 3 kilowatts per 1000 liters of reaction mixture). Thin film reaction systems may also be employed. In a particularly desirable embodiment of the invention, no materials other than the fatty acid and the propoxylated glycerin are introduced into the reaction zone; i.e., no catalyst, solvent, entrainer, or azeotropic stripping agent is present.

Referring to the accompanying FIG. 1, the feed fatty acid and propoxylated glycerin are fed to esterification batch reactor 1 via line 2. In reactor 1, the reagents are reacted under known conditions to form the desired ester, suitable conditions being temperatures of 100–250° C., preferably 180–250° C. with fatty acid being used in slight excess. During the reaction, water of reaction is continuously stripped from the reaction liquid and removed from the esterifier via line 3. Operation under vacuum or addition of nitrogen stripping gas is necessarily employed to efficiently strip the water. Upon completion of the reaction, the liquid reaction mixture is removed from reactor 1 via line 4 and worked up in accordance with known procedures.

Vapors comprised of water of reaction and volatilized fatty acid are removed during the esterification via line 3 and pass to the lower end of scrubber 5. In scrubber 5, the vapors are contacted with a scrubbing liquid which is introduced via line 6. Preferably the scrubbing contact is counter current with scrubbing liquid comprising fatty acid scrubbed previously from the vapors removed via line 3. Vapors comprised of the water of reaction from which fatty acid has been scrubbed are removed via line 7.

Essential to practice of the invention is the feature of scrubbing the esterifier vapors with warm scrubbing liquid which is maintained at a temperature above the melting point of the fatty acid removed from reactor 1. Preferably the scrubbing liquid is at a temperature of 95–130° C., more preferably 100–125° C.

In especially preferred practice, the scrubbing liquid is the same fatty acid as used in the esterification which has previously been condensed.

Figure 2:
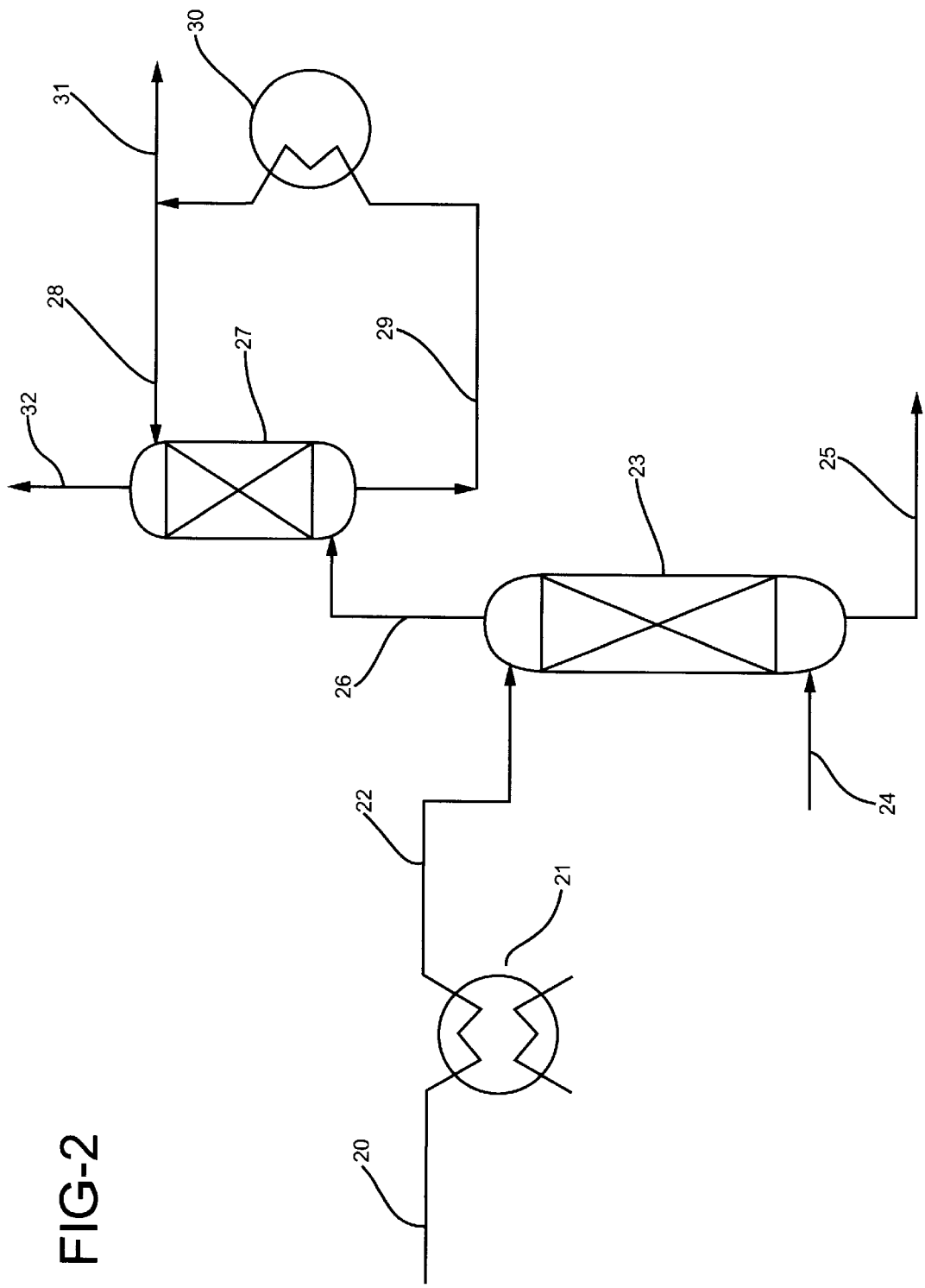

A further practice of the invention is shown in attached FIG. 2. Referring to FIG. 2, the esterification reaction mixture at the completion of the esterification as described for FIG. 1 passes via line 20 to heat exchanger 21 wherein the reaction mixture is heated to high temperature for flashing, e.g. 250–300° C., by indirect heat exchange with hot oil or high pressure steam.

The heated mixture then passes via line 22 to the upper section of flash column 23 wherein it is flashed at reduced pressure. Stripping steam or nitrogen is introduced to the lower section of column 23 via line 24. Crude esterified propoxylated glycerin is withdrawn via line 25 at the bottom of column 23 and may be further treated in accordance with known procedures.

In column 23, unreacted fatty acids are stripped from the esterification reaction mixture and overhead vapors comprised of stripping gas and fatty acids are removed via line 26 and pass to the lower section of scrubber column 27. Warm fatty acid, e.g. at 95–130° C., preferably at 100–125° C., is introduced as scrubbing liquid to the upper section of column 27 via line 28. In column 27, the great bulk of fatty acids is scrubbed from the vapor stream passing from column 23 via line 26. Scrubbing liquid passes from column 27 via line 29 to heat exchanger 30 wherein the liquid is cooled. From cooler 30 a portion of the cooled liquid returns to column 27 via line 28 while net recovered fatty acid is recovered via line 31.

Vapors from column 27, greatly reduced in fatty acid content are removed from column 27 via line 32, preferably passing to a vacuum system (not shown) and further recovery.

EXAMPLE 1

The following example illustrates the embodiment shown in FIG. 1.

The esterification reactor 1 contains 120,084 lbs of hydrogenated fatty acids from soya bean oil, 98,250 lbs of hydrogenated fatty acids from rapeseed oil and 78,643 lbs propoxylated glycerin. Nitrogen in the amount of 1654 lb/hr is sparged through line 8 into the bottom of the reactor. The contents are heated to 240° C. over a period of 3 hours and held for 6 hours at that temperature.

At the completion of the reaction the reactor contains 286,078 lbs of a mixture which is 15 wt % unreacted fatty acid, 1200 ppm of the monoester of the propoxylated glycerin, 8.5 wt % of the diester of propoxylated glycerin and the balance the triester of propoxylated glycerin.

Each hour, 144 lb of fatty acids are stripped from the reactor via line 3 by the $N_2$ along with the water made in the reaction.

The removed vapor stream is passed into the bottom of 3.5' D column 5 made of 316 stainless steel containing 3' of Beryl saddles. To the top of this column is added through line 6 12,389 lb/hr of condensed fatty acid cooled to 110° C. This fatty acid plus 143.8 additional lb/hr condensed fatty acid exits the bottom of column 5 through line 9 at 130° C. This fatty acid stream is cooled with tempered water to 110° C. in exchanger 10 and the bulk recycled through line 6 to column 5. The net fatty acid, 143.8 lb/hr, exits through line 1 and can either be recycled to esterification or returned to the fatty acid producer for recovery. The off gas exits column 5 via line 7 and contains only 0.2 lb/hr fatty acid. This gas is cooled to 40° C. in exchanger 12 to condense the water of reaction. A two phase condensate mixture is passed through line 13 and separated in vessel 14. The condensed water exits through line 15. The somewhat dried product is then compressed in a centrifugal compressor 16 from 1.05 ata to 1.3 ata and returned to the reactor through line 8.

EXAMPLE 2

The following example illustrates the embodiment shown in FIG. 2.

Through line 20 passed 29,399 lb/hr of reactor effluent which contains 15 wt % unreacted fatty acid, 1200 ppm of the monoester of the propoxylated glycerin, 8.5 wt % of the diester of propoxylated glycerin and the balance the triester of propoxylated glycerin. This stream is heated to 270° C. in exchanger 21 using hot oil or high pressure steam. Then the effluent is passed through line 22 and flashed into stainless steel column 23 at 6 mm Hg pressure. The column is 5½' D and contains 8.75' of structured packing. Into the bottom of this column is injected through line 24 1764 lb/hr high pressure steam. Crude esterified propoxylated glycerin containing 0.3 wt % fatty acid is withdrawn from the bottom of column 23 through line 6. The flow is 25,341 lb/hr. The overheads containing water and fatty acids are passed via line 26 into the bottom of column 27. To the top of column 27 through line 28 is fed 93,288 lbs/hr condensed acid cooled to 120° C. The stainless steel column 27 is 8' D and has 6' of structural packing. The stream exiting the top of column 27 containing only 10 lb/hr fatty acid is passed through line 32 to a vacuum system (not shown). The recirculated and additional condensed acid is removed from the bottom of column 27 at 140° C. via line 29. This goes to exchanger 30 and is cooled with tempered water. The net recovery of acid, 4978 lb/hr, exits through line 31 for recycle.

I claim:

1. In a process for the 10 to 24 carbon atom fatty acids esterification of propoxylated glycerin wherein a vapor stream comprised of said fatty acids is formed, the improvement of scrubbing said fatty acids from the vapor by contact with a scrubbing liquid which is maintained at a temperature above the melting point of the said fatty acids.

2. In a process for the 10 to 24 carbon atom fatty acid esterification of propoxylated glycerin wherein water of esterification is stripped as vapor from the esterification reaction zone together with volatilized 10 to 24 carbon atom fatty acid, the improvement which comprises scrubbing said fatty acid from the stripped vapor by contact with a scrubbing liquid the temperature of which is maintained above the melting point of the said fatty acid.

3. The process of claim 2 wherein the scrubbing liquid is a 10 to 24 carbon atom fatty acid liquid maintained above 100° C.

4. In a process for the 10 to 24 carbon atom fatty acids esterification of propoxylated glycerin wherein a reacted product mixture is formed comprised of esterified propoxylated glycerin and unreacted 10 to 24 carbon atom fatty acids, and said unreacted 10 to 24 carbon atom fatty acids are stripped as vapor from the reaction product mixture the improvement of scrubbing said fatty acids from said vapor by contact with a scrubbing liquid which is maintained at a temperature above the melting point of the said fatty acids.

5. The process of claim 4 wherein the scrubbing liquid is a 10 to 24 carbon atom fatty acid liquid maintained above 100° C.

\* \* \* \* \*